United States Patent [19]

Sterling

[11] 4,075,131
[45] Feb. 21, 1978

[54] CONDITIONING SHAMPOO

[75] Inventor: Craig A. Sterling, North St. Paul, Minn.

[73] Assignee: Minnesota Mining and Manufacturing Company, St. Paul, Minn.

[21] Appl. No.: 724,111

[22] Filed: Sept. 17, 1976

[51] Int. Cl.² .................. C11D 1/02; C11D 3/26; A61K 7/06

[52] U.S. Cl. .................. 252/542; 252/547; 252/548; 252/DIG. 2; 252/DIG. 13; 424/70; 424/78

[58] Field of Search .............. 252/106, 544, 547, 548, 252/DIG. 2, DIG. 13; 424/70, 71, 78, DIG. 2

[56] References Cited

U.S. PATENT DOCUMENTS

| | | |
|---|---|---|
| 3,313,734 | 4/1967 | Lang et al. .................. 252/547 X |
| 3,406,238 | 10/1968 | Freyermath et al. .................. 424/70 |
| 3,549,546 | 12/1970 | Moore .................. 252/542 |
| 3,723,325 | 3/1973 | Parran .................. 252/106 |
| 3,816,616 | 6/1974 | Anguillo et al. .................. 424/70 |
| 3,836,537 | 9/1974 | Boerwinkle et al. .................. 260/29.6 HN |
| 3,969,500 | 7/1976 | Kennerly .................. 424/10 |
| 3,980,769 | 9/1976 | Ghilardi et al. .................. 424/70 |
| 3,996,146 | 12/1976 | Tarasov et al. .................. 252/142 |

Primary Examiner—P.E. Willis, Jr.
Attorney, Agent, or Firm—Cruzan Alexander; Donald M. Sell; Richard Francis

[57] ABSTRACT

A conditioning shampoo composition especially suited for use in cleansing and conditioning human hair is comprised of an aqueous mixture of detergent and zwitterionic polymer. The detergent may either be an anionic surfactant or an amphoteric surfactant or a mixture thereof.

13 Claims, No Drawings

CONDITIONING SHAMPOO

BACKGROUND OF THE INVENTION

It has long been a desire of the cosmetic industry to produce a composition for use on human hair which would cleanse the hair and rinse out easily while imparting gloss to the hair without excessive dryness. While it has been relatively easy to produce compositions which will cleanse the hair and rinse out easily, such compositions have been deficient in one or more other areas. Some compositions leave the hair difficult to comb, rough to the hand, lacking luster and/or cause it to become unmanageable when the dry hair is combed due to the static electricity caused by excessive removal of oil from the hair.

Many of these problems are caused by the new synthetic detergents presently used to cleanse hair which not only remove dirt, but also remove a good portion of natural oils and sebum from the hair and scalp, making the hair more difficult to manage. This decreased manageability is first noticed during the actual shampooing by the hair becoming snarled and entangled and, later, after the hair has been towel-dried, when combing is attempted.

A commonly accepted method of overcoming the tangling problem is to treat the shampooed hair with a conditioning composition, after the shampoo has been rinsed from the hair. The conditioning composition will generally coat the hair shafts to reduce tangling, making wet combing easier, providing improved manageability.

The use of a separate conditioning composition after shampooing is inconvenient. Additionally, the use of a separate shampoo and conditioner adds greatly to the cost since each of these items must be packaged separately and since, in many instances, the packaging costs typically exceed the cost of the contents.

One might therefore expect combination of a known hair cleansing agent with a known hair conditioner to provide a simple solution but such combinations are more often unsuited for use on hair for any purpose. It may be possible to predict, in certain instances, whether of not certain types of detergent compositions will perform satisfactorily on human hair. It may also be possible to predict, to some degree, whether or not a particular composition will have a conditioning effect upon the hair. It is virtually impossible, however, to determine whether or not combinations of such ingredients will be compatible, even though they may have been established separately as successful candidates for use on hair. This is especially true since most hair detergents and hair conditioning agents are ionic compositions which quite often interact to form an unsuitable complex, although they may be separately useful.

Prior art conditioning compositions for use after shampooing are generally comprised of cationic resins which can not be used simultaneously with detergent compositions normally employed to cleanse hair because they are generally anionic. This same incompatibility may cause problems even when these compositions are used separately. Unless some anionic shampoos are completely rinsed from the hair (this being virtually impossible), the addition of certain cationic conditioning compositions may cause some adduct precipitation on the hair, imparting an objectionable feel to the hair. As well as this, the presence of this adduct causes increased soiling and oftentimes leaving the hair much softer than desired which may cause premature falling of subsequently applied hair styling.

U.S. Pat. No. 3,816,616 discloses one example of a unitary shampoo and conditioning composition comprised of a particular cationic polymer based upon a repeating substituted anhydroglucose and anionic detergent. Consistent with the discussion above, it is acknowledged in this patent that formulation of such material is extremely difficult because of the tendency for detergents and conditioning compositions to chemically combine and precipitate on the hair and leave an undesirable residue which has an adverse effect upon the hair.

SUMMARY OF THE PRESENT INVENTION

The present invention provides a conditioning shampoo composition which will cleanse the hair and simultaneously condition it during the shampooing process to provide improved wet combing and appearance. Hair treated with the shampoo of the invention will be clean and have excellent luster and manageability, avoiding the problems discussed above.

The conditioning shampoo of the invention is comprised of an aqueous mixture of detergent and zwitterionic polymer. The detergent may either be an anionic surfactant or an amphoteric surfactant or a mixture thereof. It may also contain other ingredients commonly used in shampoo compositions such as foam builders, protein, colorants, perfumes and the like.

In the context of the invention, the expression "zwitterionic polymer" and "zwitterionic monomer" refer to internally neutralized polymers and monomers containing a carboxylic group and an ammonium group.

DETAILED DESCRIPTION OF THE INVENTION

The zwitterionic polymers useful in practicing this invention are addition polymers which may be prepared by polymerizing certain zwitterionic monomers or by copolymerizing certain acidic monomers with basic monomers.

One means of obtaining such a zwitterionic polymer is by polymerizing zwitterionic monomers having a general formula:

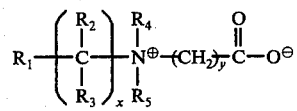

wherein, $R_1$ represents a polymerizable unsaturated group such as acrylate, methacrylate, acrylamide, or methacrylamide, subscripts "$x$" and "$y$" represent an integer from 1 to 3 inclusive to provide methylene, ethylene, or propylene groups, $R_2$ and $R_3$ represent hydrogen, methyl, ethyl, or propyl radicals, $R_4$ and $R_5$ represent a hydrogen atom or an alkyl radical with the total sum of carbon atoms in $R_4$ and $R_5$ not exceeding six.

An exemplary zwitterionic monomer having the general formula shown above which is useful in preparing zwitterionic polymers which may be used in the conditioning shampoo composition of the invention is beta-methacryloxyethyl-beta-dimethylamino-propionate betaine. Zwitterionic monomers of this type may be prepared by methods known to the art as exemplified in the disclosures of U.S. Pat. Nos. 2,744,130 and 2,777,872.

Other useful zwitterionic polymers of this type are disclosed in U.S. Pat. No. 3,836,537, incorporated herein by reference.

The aforementioned zwitterionic monomers may be homopolymerized or copolymerized with non-zwitterionic polymerizable monomers to provide useful zwitterionic polymers to reduce cost or to obtain other desirable properties. The resultant polymers retain their zwitterionic properties even when relatively large proportions of non-zwitterionic comonomer are used. Generally, the zwitterionic moiety of the resultant polymer should comprise at least, on a molar basis, about 10% of the polymer to retain the above-described properties. Typical water-soluble non-zwitterionic monomers suitable for copolymerization with the zwitterionic monomer include vinyl pyrrolidone, dimethylaminoethyl acrylate, diethylaminoethyl methacrylate, acrylic acid, methacrylic acid and maleic acid. Other non-zwitterionic monomers which are not water-soluble, such as alkyl acrylates (e.g., methyl acrylate), methacrylates, acrylamides, methacrylamides, and vinyl acetate, may also be copolymerized with the zwitterionic monomers to provide useful copolymers. However, substantially less of this type of non-zwitterionic monomer is utilized so as to maintain the requisite solubility.

Zwitterionic polymers useful in practicing the invention may also be prepared by copolymerizing certain acidic monomers with certain basic monomers. The acidic monomers are preferably substituted vinyl compounds of the general formula $CR_6H=CR_7CO_2H$ wherein $R_6$ is a hydrogen atom or a $CO_2H$ group and $R_7$ is a hydrogen atom, chlorine atom, or a methyl group. Exemplary compounds of this type include acrylic acid, methacrylic acid, maleic acid and alpha-chloroacrylic acid. The basic monomers are preferably substituted vinyl compounds of the formula $CH_2=CR_8CO-Q$, wherein $R_8$ is a hydrogen atom or a methyl group and Q is an organic radical containing a basic nitrogen containing group. Examples of such compounds include dialkylaminoalkyl methacrylates and acrylates and dialkylaminoalkyl methacrylamides and acrylamides.

For most purposes, the mole ratio of basic monomer to the acidic monomer of the aforementioned zwitterionic copolymers range from 0.6:1 to 1.5:1; and preferably 0.75 to 1:1. In the case of a difunctional monomer, suitable adjustment should be made in mole ratios to maintain a similar acid-base balance. When the basic monomer exceeds 1.5:1, the resultant compositions may be relatively unstable and their conditioning properties may decrease. Conversely, as the basic monomer content drops below 0.6:1, the conditioning properties of the resultant composition may decrease and, more importantly, the polymer itself may become exceedingly more difficult to prepare at the desired viscosity.

The zwitterionic polymers produced from acidic and basic monomers preferably will be formed of monomers of acrylic acid polymerized with monomers of dimethylaminoethyl methacrylate or diethylaminoethyl acrylate. Other useful zwitterionic polymers of this type are also described in aforementioned U.S. Pat. No. 3,836,537. Zwitterionic copolymers of the second type, besides being formed of acidic and basic monomers, may also include additional monomers which do not contain acidic or basic groups which may be added to reduce cost. Such monomers typically include lower alkyl acrylates or methacrylates, and lower alkyl acrylamides or methacrylamides. These neutral monomers, which can be water-soluble or water-insoluble, will be contained in the copolymer in proportions which do not adversely affect the solubility of the resultant copolymer. Typically, water-insoluble monomers will be a minor proportion of the resultant copolymer.

The zwitterionic polymers which are useful in the invention will have a viscosity of about 100 to 100,000 cps, when tested at 24.5 ± 0.25% non-volatiles in water (with a Brookfield viscometer, using the appropriate spindle and speed). Preferably the viscosity is about 500 to 30,000 cps. Zwitterionic polymers which have viscosities in excess of 100,000 cps tend to cause stratification of the compositions when heat-aged at 140° F. This is undesirable since the composition may separate during storage.

For use on hair, the composition of the invention comprises from about 0.5 to about 5% by weight zwitterionic polymer preferably, from about 1% to about 3%. Little conditioning effect is noted at concentrations below 0.5% zwitterionic polymer. Increasing the concentration of zwitterionic polymer beyond 5% does not result in any significant improvement in the performance of the composition. The composition may also be sold as a concentrate which can be diluted with water for use. Such concentrates may contain up to about 20% by weight zwitterionic polymer.

The detergent which comprises the other main component of the composition according to the invention is any one of many anionic surfactants or amphoteric surfactants normally employed in the cosmetic industry for cleansing human hair. The compatibility of the zwitterionic polymers described above with this wide variety of such surfactants is quite unexpected since one would expect the anionic moiety of the surfactant to combine with the cationic moiety of the zwitterionic polymers described above to form a complex which would precipitate on the hair.

Exemplary useful anionic surfactants include the alkyl benzene sulfonates having a general formula $RSO_3X$ wherein R is a biodegradable hydrocarbon group in the surfactant molecular-weight range and "X" is a cation such as potassium, sodium, ammonium, hydrogen or the like. Exemplary useful alkyl benzene sulfonates include sodium dodecyl benzene sulfonate and sodium tridecyl benzene sulfonate. Commercially available surfactants of this type are sold under the trade designations "Ardet" AB-40 (sodium dodecyl sulfonate), "Conco" AAS-50S (ammonium dodecyl benzene sulfonate), "Conco" ATR-98S (hydrogen tridecyl benzene sulfonate), "Memkal" NOBS (sodium nonyl benzene sulfonate), "Sole-Fonate" 102 (calcium dodecyl benzene sulfonate).

Also useful are the alkyl sulfate anionic surfactants, especially those derived from lauryl and myristyl alcohols which have the general formula $C_{12}H_{25}OH$ and $C_{14}H_{29}OH$ respectively. Lauryl sulfates generally give a better volume of lather while myristyl sulfates give richer lathers so a mixture of the two provides excellent surfactant compositions. Also useful are the alkyl polyethylene glycol sulfates (alkyl ether sulfates), which have extremely high foaming power. Typical of such surfactants is lauryl polyethylene glycol sulfate. Other useful anionic surfactants include the alkyl phosphates (although these are generally undesirable for environmental reasons), and the alkyl sulphosuccinates include sodium dioctyl sulphosuccinate and sodium di(tertiary)-nonyl sulphosuccinate. Longer-chain sulphosuccinates are also available but they are far less soluble in water therefore not preferred. The preferred alkyl sulphosuccinates are of the octyl and nonyl ester type. Other useful anionic surfactants include those of the secondary alkyl sulfate type, monoglyceride sulfate, isethionates, acyl sarcosines, and the like. Exemplary useful amphoteric surfactants include coco amido alkyl betaine, acyl peptides and acyl amino acids.

The contitioning shampoo composition according to the invention is generally clear, although it can be opacified by use of a suitable agent therefor. These compositions will generally be acidic, usually having a pH in the range of 4 to 7. The aqueous compositions according to the invention will generally have solid contents of from about 3 to about 65% by weight. Of these solids, approximately 1 to about 60% will comprise the anionic or amphoteric surfactant or a mixture of anionic surfactant and amphoteric surfactant. Preferably, such surfactant comprises from about 8 to 16% by weight of aqueous composition.

Up to one third of the surfactant component described above may be replaced with a cosmetically acceptable foam building nonionic surfactant. Exemplary nonionic surfactants useful in the composition of the invention include the alkyl phenoxy poly(ethyleneoxy) alkanols such as nonylphenoxypoly(ethyleneoxy) ethanol and the fatty acid alkanolamides such as coco alkanolamide The composition according to the invention may also include materials typically found as additives in conventional shampoo compositions or conditioning shampoo compositions. These include germicidal agents, antistatic agents, antidandruff agents, nonionic conditioning agents, protein additives, sequestrant additives, coloring agents, perfume additives, and preservative agents.

The conditioning shampoo composition according to the invention is preferably in the form of a liquid for use but it may also be formulated as a gel by addition of compatible thickening agents.

The following examples, in which all parts are by weight unless otherwise indicated, illustrated preparations of the zwitterionic polymers and the corresponding conditioning shampoo compositions of the invention, without limiting the scope thereof.

Preparation of a Zwitterionic Polymer Utilizing Zwitterionic Monomer

A polymerization flask fitted with a continuously operating stirrer and a thermocouple was charged with 66.7 g. of beta-methacryloxyethyl-beta-dimethylamino propionate betaine and 550 g. of water. The flask was then purged with nitrogen utilizing vacuum techniques and subsequently heated to 60° C. Ammonium persulfate (0.67 g.) catalyst in 50 g. of water was added. The flask contents were stirred at 60° C for 12 hours until the reaction was complete. The resultant clear polymer solution had a Brookfield viscosity of 102 cps (Spindle #1 at 30 rpm). This polymer is identified in the Examples below as zwitterionic polymer "A".

Preparation of Zwitterionic Polymer From Acidic and Basic Monomers

A polymerization flask fitted with a continuously operating stirrer and a thermocouple was charged with 1400 g. of deionized water and 309.8 of beta-dimethylaminoethyl methacrylate. Acrylic acid (170.2 g.) inhibited with 1000 ppm para-methoxyphenol was added, resulting in a slight exotherm which caused the temperature to rise to about 33° C. Thereafter the reaction mixture was heated to 70° C. One hour after the addition of the acrylic acid, 21.1 g. of ammonium persulfate in 120 g. of deionized water was added, causing the reaction temperature to rise rapidly to 92° C. Stirring was continued for 1 hour to complete the reaction. The resultant zwitterionic polymer solution had a Brookfield viscosity of 3300 cps at 22° C (Spindle #4, at 30 rpm). This polymer is identified in the Examples below as zwitterionic polymer "B".

EXAMPLE 1

A conditioning shampoo composition was formulated from the following components:

| Component | Parts |
|---|---|
| Anionic surfactant (triethanolammonium lauryl sulfate) | 8.75 |
| Amphoteric surfactant (coco amido alkyl betaine) | 2.5 |
| Nonionic surfactant foam booster (fatty alkanolamide) | 3.0 |
| Perfume, preservative, color, etc. | Q.s |
| Protein (trade designation "Wilson" WSPX-250) | 1.0 |
| Anti-static agent (polypropoxylated quaternary ammonium chloride) | 1.0 |
| Zwitterionic polymer ("B") | 2.0 |
| Water | Q.s to 100.0 |

While heating the water to 75° – 80° with moderate stirring, the components (except for the perfume and protein) were added and this peak temperature was maintained for an additional ten minutes. Thereafter, while continuing stirring, the mixture was cooled to 40° – 45° C whereupon the perfume was added and then to 37° C whereupon the protein was added.

The resulting conditioning shampoo was clear and homogeneous, having a pH of 5.8 – 6.5. When the shampoo was applied to the hair and lathered, the hair was cleansed as well as conditioned. The hair was left lustrous, clean and easy to comb. The formulation was stable both at room temperature and at elevated temperatures.

EXAMPLE 2

| Components | Parts |
|---|---|
| Triethanol ammonium laurylsulfate | 10.0 |
| Fatty alkanolamide | 3.0 |
| Perfume, preservatives and color | Q.s. |
| Protein | 1.0 |
| Polypropoxylated quaternary ammonium chloride | 1.0 |
| Zwitterionic polymer ("B") | 2.0 |
| Water | Q.s. to 100.00 |

A homogeneous conditioning shampoo having a pH of 6.5 was prepared of the components shown above following the procedure set forth in Example 1. This composition performed very well, leaving the hair clean, soft and easy to comb.

Evaluation

The effectiveness of the conditioning shampoo compositions of the invention was readily determined by two tests. The first test evaluated the wet combing ability of the hair. The second evaluated the softening effect or loss of holding power of subsequent hair sets.

In the wet combing test, two hair swatches, a 2.0 gram, 15 cm virgin brown human hair swatch and a 2.0 gram, 15 cm bleached human hair swatch, were first cleansed by shampooing twice with 1 ml of a control anionic shampoo (identified as Control "A" hereinafter). Control "A" was produced by diluting Control "A" concentrate described below with eight volumes of tap water.

| CONTROL "A" CONCENTRATE | |
|---|---|
| Component | Parts |
| Coco alkanol amide | 37.5 |
| Sodium lauryl sulfate | 23.5 |
| Sodium coconut ether sulfate | 18.8 |
| Propylene glycol | 10.0 |
| Coco amido alkyl betaine | 10.0 |
| Perfume | 0.2 |
| Citric acid | .98 |
| Water | Q.s. to 100.00 |

Each swatch was combed once, shampooed and rinsed under tepid running water.

One set of the cleansed hair swatches was evaluated with 1 ml of Control "A" shampoo using this as a standard for comparing the test conditioning shampoo compositions. The other set of cleansed hair swatches was treated with 1 ml of the test conditioning shampoo being evaluated. In each case, after rinsing with tepid running water without combing, the excess water was removed from each of the swatches by pressing between the thumb and index finger. The swatches were then combed wet using a fine-tooth comb by a person experienced in the art and evaluated on a scale from zero to 5. An evaluation of zero meant the swatch could not be combed, while an evaluation of 5 meant the swatch was very easily combed. Control swatches shampooed with the Control "A" anionic shampoo composition without zwitterionic hair conditioner had wet comb out ratings of 2 for virgin brown human hair and zero to 1 for the bleached hair. A commercially acceptable shampoo will condition virgin brown human hair to provide a comb-out rating of 3 and of 2 for bleached hair. The ratings of the evaluated compositions are reported in Table II hereinafter.

The test method for evaluating the effect of the conditioning shampoo composition on subsequent hair sets consisted of first cleansing ten 2g., 15 cm tresses of natural brown human hair for each composition being tested with Control "A" anionic shampoo. This cleansing was accomplished by dipping the tresses into the shampoo and combing 25 times and then rinsing the tresses by combing 25 times under tepid running water. The excess water was then removed by pressing the tresses between the thumb and forefinger. Ten of the cleansed tresses for each composition being evaluated were dipped into the conditioning shampoo composition being evaluated and lathered by combing 25 times. If the composition being evaluated contained no shampoo, the tresses were dipped, combed once, dipped again, combed once more, and then dipped a third time, this time leaving the tresses in the solution for two minutes. The tresses, subsequent to their individual treatment, were rinsed thoroughly in tepid running water and the excess water squeezed from the tresses.

The tresses were then subsequently treated with a commercial setting lotion (sold by the 3M Company under the trade designation "Body Bond") comprised of zwitterionic polymer to determine the softening effect or loss of holding power caused by the conditioning shampoo. This treatment was accomplished by first dipping each of the tresses three times in the commercial setting lotion and combing once. This dipping was repeated with the comb being rinsed with water and tapped dry before combing. The rinsed tresses were then combed using different portions of the comb to remove excess setting lotion. Thereafter the tresses were set on 2.53 cm (1 inch) plastic rollers, secured with hair clips, and dried at 60° C for four hours. The rollers were removed after this time and the tresses were brushed five times with a nylon bristle brush. The tresses were then recurled with the fingers and the initial length ($L_i$) of each curl was measured. The set hair swatches were then placed in a 85–90% constant humidity chamber for one hour, then removed and the resultant length of the curl ($L_f$) measured.

Curl retention is the average of the curl retentions of the ten hair swatches for each material being evaluated and is calculated as follows:

Curl Retention (CR) = $(6-L_f)/(6-L_i) \times 100$.

Relative curl retention with respect to Control "A" as a shampoo is obtained by dividing the curl retention of the composition being considered by that obtained by evaluating Control "A" shampoo and multiplying by 100.

Evaluation of Example 2, Control "A" anionic shampoo and a well-known commercial quaternary polymer creme rinse identified below as Control "B" (sold under the trade designation "Zotos Pine Balsam" by Zotos International of Darien, Conn.), when tested as described above, produced the results shown in Table I below.

TABLE I

| Example No. | Relative Curl Retention |
|---|---|
| Example 2 | 105 |
| Control A | 100 |
| Control B | 87 |

Table II sets forth additional examples of conditioning shampoo compositions, including those of Examples 1 and 2, together with their evaluation results of the wet combing test. Examples 3–24 were made in accordance with the description of the composition of Example 2, except for substitution of the zwitterionic polymer for that mentioned in the table. The composition of each of the zwitterionic polymers employed in these examples is set forth in this table as is its reaction temperature and amount of catalyst. Two of the examples fall outside of the scope of the invention because they do not include zwitterionic polymer as defined in the claims in that certain of these polymers are not composed of comonomer in the specified mole ratio. The examples not conforming to the invention, shown for purposes of comparison, are identified in Table II with an asterisk (*).

TABLE II

| Ex. No. | Zwitterionic Polymer Composition | | Reaction Parameters | | Polymer Properties | | | Shampoo Evaluation[18] | |
|---|---|---|---|---|---|---|---|---|---|
| | Monomers | Mole Ratio | Temp.° C[1] | Cat.[2]% | Non-Volatiles % | Viscosity[3] CPS | Spindle | RPM | Brown Hair | Bleached Hair |
| 1 | DMAEMA[4] betaine | homopolymer | 60 | 1 | 7.7 | 102 | 1 | 30 | 4+ | 3—[19] |

TABLE II-continued

| Ex. No. | Zwitterionic Polymer Composition Monomers | Mole Ratio | Reaction Parameters Temp.°C[1] | Cat.[2]% | Non-Volatiles % | Polymer Properties Viscosity[3] CPS | Spindle | RPM | Shampoo Evaluation[18] Brown Hair | Bleached Hair |
|---|---|---|---|---|---|---|---|---|---|---|
| 2 | DMAEMA:AA[5] | 45.5:54.5 | 70 | 4.4 | 25.2 | 3,300 | 4 | 30 | 4 | 3 |
| 3 | DMAEMA:AA | 60:40[6] | 70 | 0.5 | 25.3 | 10,400 | 4 | 30 | 2 | 2 |
| 4 | DMAEMA:AA | 51:49[6] | 69 | 0.6 | | | | | 3 | 2 |
| 5 | DMAEMA:AA | 50:50 | 70 | 4.4 | 25.1 | 5,080 | 4 | 30 | 3.5 | 3 |
| 6 | DMAEMA:AA | 48:52 | 70 | 4.2 | 24.8 | 6,580 | 4 | 30 | 3.5 | 3 |
| 7 | DMAEMA:AA | 45:55 | 70 | 2.5 | 25.0 | 13,440 | 4 | 30 | 4 | 3+ |
| 8 | DMAEMA:AA | 45:55 | 70 | 1.5 | 24.9 | 138,000 | F | 6 | 3 | 2 |
| 9 | DMAEMA:AA | 43:57 | 70 | 2[7] | 25.1 | 28,600 | 4 | 12 | 4 | 3 |
| 10 | DMAEMA:AA | 40:60 | 80 | 3.75 | 25.3 | 2,720 | 4 | 30 | 2+ | 1− |
| 11* | DMAEMA:AA | 35:65 | 83 | 3.75 | 25.6 | 6,840 | 4 | 30 | 1+ | 1 |
| 12 | DMAEMAA[8]:AA | 45.5:54.5 | 73 | 3.75 | 22.1 | 290 | 2 | 30 | 2+ | 2 |
| 13 | DMAEA[9]:AA | 45.5:54.5 | 73 | 3.75 | 12.2 | 106 | 1 | 30 | 3− | 1− |
| 14 | DEAEA[10]:AA | 45.5:54.5 | 73 | 3.75 | 11.8 | 109 | 1 | 30 | 3 | 2 |
| 15 | DMAEMA:MAA[11] | 45.5:54.5 | 73 | 3.75 | 11.5 | 3,860 | 4 | 30 | 2+ | 1− |
| 16 | DMAEAA[12]:AA | 45.5:54.5 | 73 | 3.75 | 6.2 | 24 | 1 | 30 | 3+ | 2 |
| 17 | DEAEMA[13]:AA | 45.5:54.5 | 73 | 3.75 | 18.7 | 2,580 | 4 | 30 | 3− | 2− |
| 18 | DMAEMA:AA:Q-5[14] | 40.9:49.1:10 | 73 | 3.75 | 25.5 | 4,060 | 4 | 30 | 1 | 2+ |
| 19 | DMAEMA:AA:Q-5[14] | 36.4:43.6:20 | 73 | 3.75 | 26.4 | 1,256 | 3 | 30 | 2+ | 0 |
| 20 | DMAEMA:AA:Q-5 | 27.3:32.7:40 | 73 | 3.75 | 25.6 | 200 | 2 | 30 | 3− | 2 |
| 21 | DMAEMA:AA:M-MA[15] | 43.2:51.8:5 | 73 | 3.75 | 24.1 | 2,820 | 4 | 30 | 2+ | 0 |
| 22 | DMAEMA:AA:M-MA[15] | 40.9:49.1:10[16] | 73 | 2.65 | 24.6 | 133 | 1 | 30 | 2− | 2− |
| 23 | DMAEMA:MA[17] | 62.6:37.4 | 73 | 3.75 | 24.6 | 60 | 1 | 30 | 2 | 2− |
| 24* | DMAEMA:MA[17] | 45.5:54.5 | 73 | 3.75 | 23.9 | 31.2 | 1 | 30 | 3− | 2+ |
| 25 | No polymer | | | | | | | | 1+ | 1 |
| A[20] | | | | | | | | | 2 | 0–1 |

[1]Temperature when catalyst is added.
[2]Weight percent $(NH_4)_2S_2O_8$ catalyst used in reaction
[3]Brookfield viscosity, 22 C.
[4]dimethylaminoethyl methacrylate
[5]acrylic acid
[6]excess amine neutralized with HCl
[7]0.5% post catalyst and 0.5% TGA present
[8]dimethylaminoethyl methacrylamide
[9]dimethylaminoethyl acrylate
[10]diethylaminoethyl acrylate
[11]methacrylic acid
[12]dimethylaminoethyl acrylamide
[13]diethylaminoethyl methacrylate
[14]trimethyl β methacryloxy ethyl ammonium methyl sulfate
[15]methyl methacrylate
[16]ethanol solvent, azobisisobutyronitrile catalyst
[17]maleic acid
[18]shampoos prepared as in Example 3
[19]evaluated on head rather than by use of hair swatches
[20]Control A

EXAMPLES 26 – 35

Examples 26–35 were prepared by mixing at 75° C various surfactants with a preferred zwitterionic polymer (45.5:54.5 mole % DMAEMA:AA) to determine the effect of the surfactant type on the conditioning properties. Each example contained 2% by weight zwitterionic polymer and 11.75% by weight of surfactant shown in Table II. The cooled solutions were evaluated as described previously with respect to the wet combing properties of shampooed hair tresses. The data appears in Table II.

TABLE II

| Example | Surfactant (type) | Trade Name | Wet Comb Out Brown Hair | Bleached Hair | pH |
|---|---|---|---|---|---|
| 26 | Sodium tallow soap (anionic) | — | 4 | 3+ | 9.05 |
| 27 | Sodium lauryl ether sulfate (anionic) | "Steol" CS-460 | 3+ | 3− | 5.25 |
| 28 | Coco amido alkyl betaine (amphoteric) | "Tego" betaine-C | 3− | 3− | 4.8 |
| 29 | Coco amido sulfo betaine (amphoteric) | "Lonzaine" CS | 3+ | 3 | 5.45 |
| 30 | Di-sodium salt of 2-undecyl-1-(ethyl-B-oxyethanoic acid)-1-(ethanoic acid) imidazoline (amphoteric) | "Amphoterge" K-2 | 4 | 1+ | 8.9 |
| 31 | Lauryl dimethyl amine oxide (amphoteric) | "Ammonyx" LO | 3+−4− | 3− | 7.15 |
| 32 | Nonylphenolethoxylate (nonionic) | "Igepal" CO 630 | 2− | 2 | 4.85 |
| 33 | Lauryl diethanol amide (nonionic) | "Unamide" JJ35 | 4 | 3 | 7.75 |
| 34 | Sodium lauryl sulfate (8.75%) (anionic) Coco amido alkyl betaine (3.0%) (amphoteric) | "Sipon" Lt-6 "Tegobetaine" C | 4 | 3 | 5.75 |
| 35 | No surfactant | — | 2+ | 1+ | 4.7 |

What is claimed is:

1. A conditioning shampoo composition which consists essentially of from about 1% to about 60% by weight anionic or amphoteric surfactant and at least about 0.5% by weight zwitterionic polymer, said polymer containing at least 10% on a molar basis of zwitterionic moiety, having a viscosity of about 100 to 100,000 cps, when tested at 24.5 ± 0.25% non-volatiles in water (with a Brookfield viscometer, using the appropriate spindle and speed) and being selected from a group consisting of (A) polymers of carboxy betaines having the repeating formula

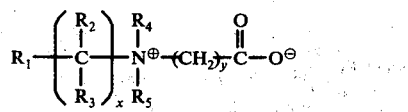

wherein, $R_1$ represents a polymerizable unsaturated group, x and y represent integers from 1 to 3 inclusive, $R_2$ and $R_3$ represent hydrogen, methyl, ethyl or propyl radicals, $R_4$ and $R_5$ represent a hydrogen atom or an alkyl radical with the total carbon atoms in $R_4$ and $R_5$ not exceeding six, and (B) copolymers of monomers (1) and (2), shown below:
(1) substituted acidic vinyl compounds having the general formula $CR_7H=CR_8CO_2H$ wherein $R_7$ represents a hydrogen atom or a carboxylic acid group and $R_8$ represents a hydrogen atom, a chlorine atom or a methyl group, and
(2) substituted basic vinyl compounds having the general formula $CH_2=CR_6COQ$ wherein $R_6$ represents a hydrogen atom or a methyl group and Q is an organic radical containing a basic nitrogen-containing group, wherein the mole ratio of basic monomer to acidic monomer in said copolymer is from 0.6:1 to 1.5:1, except where $R_7$ is $CO_2H$, the mole ratio is 1.2:1 to 3:1.

2. The composition of claim 1 wherein said zwitterionic monomer is beta-methacryloxyethyl-beta-dimethylaminopropionate betaine.

3. The composition of claim 1 wherein said acidic vinyl compound monomer is selected from the group consisting of acrylic acid, methacrylic acid, maleic acid and alphachloroacrylic acid.

4. The composition of claim 1 wherein said basic vinyl compound monomer is selected from the group consisting of dialkylaminoalkyl methacrylates, dialkylaminoalkyl acrylates, dialkylaminoalkyl methacrylamides and dialkylaminoalkyl acrylamides.

5. The composition of claim 1 wherein said zwitterionic copolymer is obtained by polymerizing acrylic acid with dimethylaminoethyl methacrylate or diethylaminoethyl acrylate.

6. The composition of claim 1 wherein said zwitterionic polymer comprises from about 0.5 to about 5% by weight of said composition.

7. The composition of claim 1 wherein said anionic or amphoteric surfactant is replaced up to one third of its weight with a cosmetically acceptable foam building nonionic surfactant.

8. The composition of claim 7 wherein said non-ionic surfactant is selected from the group consisting of alkyl phenoxy poly(ethyleneoxy) alkanol and fatty acid alkanol amides.

9. The composition of claim 1 wherein there is also contained protein.

10. A method of cleansing and conditioning the hair and scalp by applying an aqueous composition as defined in claim 1 to the hair and scalp, working it to a lather and rinsing.

11. A method of cleansing and conditioning the hair as set forth in claim 10 wherein said zwitterionic polymer is present in an amount of from about 0.5 to about 5% by weight in said composition.

12. The composition of claim 1 wherein said (A) carboxy betaine polymer also contains non-zwitterionic monomer selected from the group consisting of acrylic and methacrylic acid, vinyl pyrrolidone, dialkylaminoalkyl acrylates, dialkylaminoalkyl methacrylates, quaternary ammonium acrylates, quaternary ammonium methacrylates, alkyl acrylates, alkyl methacrylates, acrylamides, methacrylamides, and vinyl acetate.

13. The composition of claim 1 wherein said (B) copolymer also contains non-zwitterionic monomer selected from the group consisting of vinyl pyrrolidone, dialkylaminoalkyl acrylates, dialkylaminoalkyl methacrylates, quaternary ammonium acrylates, quaternary ammonium methacrylates, alkyl acrylates, alkyl methacrylates, acrylamides, methacrylamides, and vinyl acetate.

* * * * *